United States Patent
Peck et al.

(12)

(10) Patent No.: US 6,218,114 B1
(45) Date of Patent: Apr. 17, 2001

(54) METHODS FOR DETECTING DIFFERENTIALLY EXPRESSED GENES

(75) Inventors: Konan Peck; Jeremy J. W. Chen; Pan-Chyr Yang, all of Taipei (TW); Reen Wu, Davis, CA (US); Fu Chang, Hsin Chu (TW); Yi-Wen Chu, His Chih (TW); Cheng-Wen Wu, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/049,569

(22) Filed: Mar. 27, 1998

(51) Int. Cl.$^7$ .............. C12Q 1/68; C07H 21/02; C07H 21/04; C12N 15/00
(52) U.S. Cl. ............ 435/6; 536/23.1; 536/24.3; 935/76; 935/77; 935/78
(58) Field of Search .............. 435/6; 536/23.1, 536/24.3; 935/76, 77, 78

(56) References Cited

U.S. PATENT DOCUMENTS

| | | | | |
|---|---|---|---|---|
| 4,825,388 | * | 4/1989 | Dailey et al. | 364/518 |
| 4,996,142 | * | 2/1991 | Al-Hakim et al. | 435/6 |
| 5,316,906 | * | 5/1994 | Haugland et al. | 435/4 |
| 5,338,843 | * | 8/1994 | Quante et al. | 540/222 |
| 5,445,934 | | 8/1995 | Fodor et al. | 435/6 |
| 5,480,791 | * | 1/1996 | Fujita et al. | 435/196 |
| 5,595,726 | | 1/1997 | Magda et al. | 424/9.61 |
| 5,690,894 | | 11/1997 | Pinkel et al. | 422/68.1 |
| 5,700,637 | | 12/1997 | Southern | 435/6 |
| 5,721,102 | | 2/1998 | Vo-Dinh | 435/6 |
| 5,723,320 | | 3/1998 | Dehlinger | 435/91.1 |
| 5,800,992 | * | 9/1998 | Fodor et al. | 435/6 |
| 5,804,382 | * | 9/1998 | Sytkowski et al. | 435/6 |
| 6,040,138 | * | 3/2000 | Lockhart et al. | 435/6 |

OTHER PUBLICATIONS

The Sigma Catalog, p. 82 (1993 Edition).*
Bers et al., "Protein and Nucleic Acid Blotting and Immunobiochemical Detection", Bio Techniques 3:276–288, 1985.
Lee et al., "A Simplified High Speed Multicolor Immunoblotting Method", Analytical Biochemistry 175:30–35, 1988.
Liang et al., "Differential Display of Eukaryotic Messenger RNA by Means of the Polymerase Chain Reaction", Science 257:967–971, 1992.
Schena et al., "Quantitative Monitoring of Gene Expression Patterns with a Complementary DNA Microarray", Science 270:467–470, 1995.
Velculescu et al., "Serial Analysis of Gene Expression", Science 270:484–487, 1995.

* cited by examiner

Primary Examiner—Ethan Whisenant
(74) Attorney, Agent, or Firm—Fish & Richardson P.C.

(57) ABSTRACT

The invention relates to a method of detecting a differentially expressed gene in a first sample of nucleic acids representing a first population of RNA transcripts and a second sample of nucleic acids representing a second population of RNA transcripts. The nucleic acids in the samples are labled with a member of specific binding pair, and the labeled nucleic acids in each sample are then hybridized to an excess of copies of a gene-specific sequence. The hybridized nucleic acids in each sample are further labeled by binding a second member of the specific binding pair to the first member, in which the second member has an activity to convert a chromogenic substrate into a chromogen. As a result of contacting the second member with the chromogenic substrate, the chromogenic substrate is converted into the chromogen. A difference in the amounts of chromogen produced from assaying the two samples indicate that the gene-specific sequence is differentially expressed in the samples.

12 Claims, 1 Drawing Sheet

METHODS FOR DETECTING DIFFERENTIALLY EXPRESSED GENES

BACKGROUND OF THE INVENTION

Exploring regulated gene expression in complex biological systems often requires the ability to monitor expression of a large number of expressed genes in a simple, inexpensive assay. Nucleic acid hybridization on filter membranes (e.g., nitrocellulose or nylon) are familiar to most researchers practicing molecular biology, as is autoradiography, which has been the standard detection method for measuring gene expression via hybridization. True-color signals generated by chromogen-converting enzymes yield more information than just intensity, the focus of many known detection methods. Based on how the human eye works, true color can be separated into three components: hue, saturation, and brightness. Alternatively, true color can be separated into the subtractive primary colors cyan, magenta, and yellow. A slight change in any of the three components results in a difference often observable by the human eye.

SUMMARY OF THE INVENTION

In general, the invention relates to a method of detecting a differentially expressed gene by providing a first sample of nucleic acids representing a first population of RNA transcripts and a second sample of nucleic acids representing a second population of RNA transcripts. The nucleic acids in the first sample is labeled (e.g., end-labeled or internally labeled) with a first member of a first specific binding pair, and the nucleic acids in the second sample is labeled (e.g., end-labeled or internally labeled) with a first member of a second specific binding pair. The labeled nucleic acids in each sample are then hybridized to an excess of copies of a gene-specific sequence from a DNA library. The hybridized nucleic acids in each sample are further labeled by binding a second member of the first specific binding pair to the first member of the first specific binding pair and binding a second member of the second specific binding pair to the first member of the second specific binding pair, in which the second member of the first specific binding pair has an activity to convert a first chromogenic substrate (e.g., X-gal) into a first chromogen and the second member of the second specific binding pair has an activity to convert a second chromogenic substrate (e.g, Fast Red/Naphthol AS-MX) into a second chromogen. The first chromogenic substrate and the second chromogenic substrate are contacted with the second member of the first specific binding pair and the second member of the second specific binding pair, respectively. As a result, the first chromogenic substrate and the second chromogenic substrate are converted into the first chromogen and the second chromogen, respectively, and the amounts of the first chromogen and the second chromogen relative to each other are determined. A difference in the amounts of the first chromogen and the second chromogen indicates that the gene-specific sequence is differentially expressed in the first population of RNA transcripts and the second population of RNA transcripts.

In one variation of the assay, the nucleic acids in the first sample and the nucleic acids in the second sample are mixed together after the nucleic acids in the first sample are labeled with the first member of the first specific binding pair and the nucleic acids in the second sample are labeled with the first member of the second specific binding pair. In this case, the first members of the first and second specific binding pairs are different. For example, the first member of the first specific binding pair includes biotin and the first member of the second specific binding pair includes digoxigenin. In addition, the color of the first chromogen is different from the color of the second chromogen.

Alternatively, the nucleic acids in the first sample and the nucleic acids in the second sample are not mixed together and the color of the first chromogen can be the same as the color of the second chromogen.

The invention also relates to a method of determining a copy number of a gene transcript by providing a sample nucleic acid representing the gene transcript and adding a predetermined amount of a known nucleic acid to the sample nucleic acid. The nucleic acids in the sample are stoichiometrically labeled with a first member (e.g., biotin or digoxigenin) of a specific binding pair and separately hybridized to (1) an excess of copies of a sequence specific to the gene transcript and (2) an excess of copies of a sequence specific to the known nucleic acid. The hybridized sample nucleic acid and known nucleic acid are labeled by binding a second member of the specific binding pair to the first member of the specific binding pair, the second member of the specific binding pair having an activity to convert a chromogenic substrate (e.g., X-gal or Fast Red TR/Naphthol AS-MX) into a chromogen. The chromogenic substrate is then contacted with the second member of the specific binding pair, thereby converting the chromogenic substrate into the chromogen. The copy number of the gene transcript in the sample is determined by comparing (1) the amount of chromogen produced from hybridizing the labeled sample nucleic acid to an excess of copies of a sequence specific to the gene transcript to (2) the amount of chromogen produced from hybridizing the labeled known nucleic acid to an excess of copies of a sequence specific to the known nucleic acid.

The specific binding pairs described can be any combination of at least two molecules which bind to each other with high specificity and, preferably, with high affinity and avidity. Such pairs are well known in the art, including biotin/streptavidin.

The methods of the invention require that a second member of each specific binding pair contain an activity that can convert a chromogenic substrate into a chromogen. For example, if streptavidin is the second member of a specific binding pair, streptavidin can further contain a β-galactosidase enzyme fused to the streptavidin moiety. The β-galactosidase activity would then convert the relatively colorless chromogenic substrate X-gal into a bluish chromogen. Other suitable activities are well known in the art, including alkaline phosphatase and horseradish peroxidase.

Other features or advantages of the present invention will be apparent from the following drawings, detailed description, and claims. All references cited herein are incorporated by reference.

DETAILED DESCRIPTION

Figure 1:
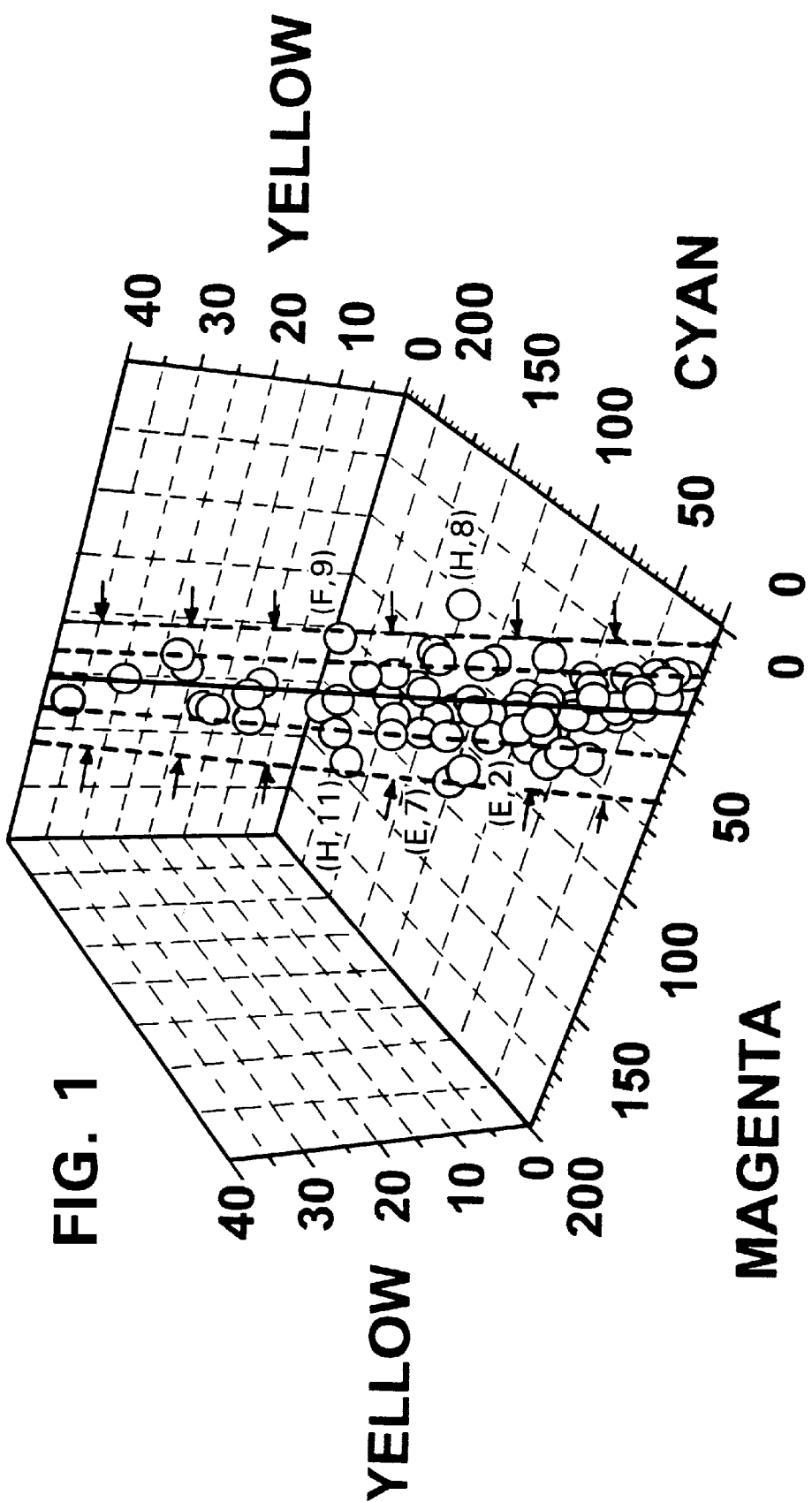
FIG. 1 is a scatter plot of the spots on a membrane produced from mixed chromagens of different colors in a method of the invention.

This invention relates to a method of detecting differentially expressed genes in two or more mRNA sources. The invention also includes a method of determining the copy number of a gene transcript. Integral to both methods is the conversion of at least one chromogenic substrate into a chromogen as the indicator of differential gene expression or transcript copy number.

Contemplated within the scope of this invention is the use of the claimed methods in a microarray format. Such arrays can be constructed on membranes (e.g., nylon or nitrocellulose membranes) or any other solid support including silicon chips. The chromogen produced in the methods of this invention is preferably detected by digitizing an image of the array, but other methods of detection can also be used. For example, the production of a specific chromogen may be detected by mass spectrometry.

Without further elaboration, it is believed that one skilled in the art can, based on the above disclosure and the examples described below, utilize the present invention to its fullest extent. The following examples are to be construed as merely illustrative of how one skilled in the art can practice the claimed methods and are not limitative of the remainder of the disclosure in any way.

EXAMPLE 1

This example compares the useful detection range of chemiluminescent Northern blotting and chromogenic detection in a microarray format and illustrates how the claimed methods can be used to quantitate a specific transcript copy number.

As a first step, the ability to carry out chromogenic detection on a microarray was tested. An arraying machine fitted with stainless steel pins spotted double-stranded cDNA fragments onto a positively charged nylon membrane (Boehringer Mannheim, Mannheim, Germany). The arraying machine was a personal computer controlled XYZ translation system (Newport Inc., Fountain Valley, Calif., Model PM500) outfitted with teflon-coated steel pins for sample delivery. The arraying system was capable of placing 100 $\mu$m diameter spots on nylon membranes with spots spaced 150 $\mu$m apart. Position resolution of the spots was better than 0.1 $\mu$m. With this capacity, approximately 85,000 gene transcripts can be placed on a piece of nylon membrane measuring 35 mm by 55 mm by using a 24-pin arraying tool.

To compare the dynamic range (the useful range of output values) of chromogenic detection with chemiluminescent Northern blotting, various pre-determined amounts (9.4× $10^6$, 1.9×$10^7$, 3.8×$10^7$, 7.5×$10^7$, 1.5×$10^8$, 3×$10^8$, 6×$10^8$, and 1.2×$10^9$ molecules) of poly-adenylated rbcL RNA were doped in an aliquot of mRNA extract of CL1-0 cells (a human lung adenocarcinoma cell line), and the doped samples were individually deposited on nylon membranes. The rbcL (Ribulose 1,5-bisphosphate carboxylase large subunit) gene is a plant gene isolated from tobacco. The gene was cloned into pBluescript II (S/K-) vector (Stratagene, La Jolla, Calif.) and amplified using two universal PCR primers, 5'-TAGAACTAGTGGATCCCCCGGGCTG-3' (SEQ ID NO:1) and 5'-TCACTATAGGGCGAATTGGGTACCG-3' (SEQ ID NO:2), which were near the EcoR I and Xho I flanking the gene insert in the plasmid. The PCR conditions were as following: first cycle, 94° C. for 5 min, 68° C. for 5 min; second to the seventeenth cycle, 94° C. for 30 sec, 68° C. for 5 min; eighteenth to thirty-fifth cycle, 94° C. for 30 sec, 68° C. for 5 min with a 15 sec increment per cycle. The PCR was carried out in a 100 $\mu$l reaction mixture containing 10 mM Tris-HCl (pH 8.8), 1.5 mM $MgCl_2$, 50 mM KCl, 0.1% Triton X-100, 200 $\mu$M dNTP, 0.2 $\mu$M of each primer, and 2 $\mu$l of thermostable DNA polymerase (Elongase, BRL). The PCR products in plates were placed in microtiter plates evaporation at 95° C. sufficient to obtain a concentration of 2–3 $\mu g/\mu l$ before spotting onto a nylon membrane.

For chromogenic detection, a panel of 93 cDNA fragments and three control plant genes (rbcL, rca [RUBISCO activase precursor], and lhc I [Photosystem I light-harvesting chlorophyll a/b-binding protein]), were amplified and deposited on a piece of nylon membrane as hybridization targets. To comply with the terms commonly used in the hybridization art, "probes" refers to the free, labeled DNA molecules in the hybridization solution while "targets" refers to DNA molecules immobilized on a solid substrate, in this case, a nylon membrane. To prepare hybridization probes, selected IMAGE cDNA clones (obtained from IMAGE consortium as described in Lennon et al., Genomics 33:151–152 [1996] through its distributor, Research Genetics, Huntsville, Ala.) and control plant genes were individually amplified by PCR to serve as probes.

These genes or cDNA clones were deposited onto 96-well microtiter plates and amplified by PCR using primers specific to the individual gene's library construct. The PCR conditions were as following: first cycle, 94° C. for 5 min, 60° C. for 30 sec, 72° C. for 3 min; second to thirty-fifth cycle, 94° C. for 30 sec, 60° C. for 30 sec, 72° C. for 3 min; and 72° C. for 10 min. The primers for PCR amplification of the cDNA clones were: 5'-AGGAAACAGCTATGACCATGATTACGC-3' (SEQ ID NO:3) and 5'-GGTTTTCCCAGTCACGACGTTGTAA-3' (SEQ ID NO:4) for Lafmid BA vectors, 5'-TACGACTCACTATAGGGAATTTGGCC-3' (SEQ ID NO:5) and 5'-GCCAGTGCCAAGCTAAAATTAACCC-3' (SEQ ID NO:6) for pT7T3D-Pac vectors, along with the universal primers described above.

The amplified cDNA fragments were labeled with digoxigenin-ll-dUTP by random priming. 1 $\mu$g of the cDNA fragments and 4 $\mu$g of random hexamer were mixed and denatured at 98° C. for 10 min before chilling on an ice/salt/ethanol mixture for 3 min. The labeling reaction was performed in a 20 $\mu$l solution containing 200 mM of HEPES buffer (pH 6.6), 50 mM Tris-HCl, 5 mM $MgCl_{2,}$ 2 mM DTT, 200 $\mu$g/ml of BSA, 100 $\mu$M each of DATP, dCTP, dGTP, 65 $\mu$M of dTTP, 35 $\mu$M of digoxigenin-11-dUTP, and 2 units of Klenow DNA polymerase (Boehringer Mannheim). The reaction mixture was incubated at room temperature for 1 hour and precipitated by ammonium acetate and ethanol.

For Northern blotting with chemiluminescent detection, various amounts of rbcL mRNA, mRNA of other control plant genes, or selected IMAGE cDNA fragments were each combined with 1 $\mu$g of mRNA extracted from CL1-0 cells. The mixtures were individually spotted on a piece of nylon membrane, and the mRNA was cross-linked to the nylon membrane by UV irradiation. The membrane was pre-hybridized in hybridization buffer (6×SSPE, 5×Denhardt's reagent, 0.2% SDS, 0.5% BM blocking reagent [Boehringer Mannheim], and 50 $\mu$g/ml salmon sperm DNA) at 68° C. for 1 hour. Specific hybridization conditions will, of course, differ from one assay to another, depending on the specific nucleic acids used in the assay. Hybridization procedures and reagents used therein are further described in Sambrook et al., Molecular Cloning: A Laboratory Manual, 2nd ed., Cold Spring Harbor Laboratory Press (1989).

Multiple Northern dot-blottings were performed, each utilizing a different probe representing either rbcL, rca, or selected IMAGE cDNA fragments at a concentration of 2 ng per ml of hybridization buffer. The reaction mixtures were sealed with the membranes in hybridization bags and incubated at 68° C. for 8–12 hours. The membranes were then washed 2 times at room temperature with 2×SSC containing 0.1% SDS for 5 min each, followed by 3 washes with 0.1×SSC containing 0.1% SDS at 65° C. for 20 min each.

The membranes were then blocked in 1×BM blocking reagent for 30 min at room temperature. Anti-DIG-alkaline phosphatase conjugates were diluted 15,000-fold in blocking buffer (0.1 M maleic acid, 0.15 M NaCl, and 0.3% Tween 20 at pH 7.5) containing 0.5×BM blocking reagent and incubated with the membranes at room temperature for 45 min. The membranes were washed with blocking buffer three times for 10 min each and equilibrated with chemiluminescence substrate buffer containing 0.1 M Tris-HCl (pH 9.5), 0.1 M NaCl, and 50 mM $MgCl_2$ at room temperature for 5 min before being placed in the developing substrate solution (ECL Gene Image System, Amersham, Buckinghamshire, UK) for 3–5 min, according to the manufacturer's instructions. The membranes were then removed from the developing solution and exposed to X-ray film (Hyperfilm ECL, Amersham, Buckinghamshire, UK). The image on the X-ray film was then digitized by a flatbed scanner (Scanjet 4 c, Hewlett Packard).

Ten solutions each containing mRNA extract of CL1-0 cells and different amounts of rbcL molecules ($6 \times 10^7$, $1.2 \times 10^8$, $2.4 \times 10^8$, $4.8 \times 10^8$, $7.2 \times 10^8$, $9.6 \times 10^8$, $1.2 \times 10^9$, $1.44 \times 10^9$, $1.68 \times 10^9$, and $1.92 \times 10^9$ molecules) were labeled with biotin and used as hybridization probes. The GAPDH gene was used as an internal control to normalize the minor differences among different hybridization reactions. The results clearly demonstrate that the chromogenic detection method had better dynamic range of quantitation than the chemiluminescent Northern blotting method. For example, detection by Northern analysis resulted in an exponential relationship between the number of RBCL molecules and the X-ray film density, whereas chromogenic detection resulted in a linear relationship between the number of RBCL molecules and the intensity of chromogen dots. In addition, the Northern had roughly two orders of magnitude in dynamic range while the chromogenic detection method reached three orders of magnitude in dynamic range.

In order to determine which method is more accurate, known amounts of rca and rbcL genes were spiked into the cellular mRNA extract of CL1-0. The results shown in Table I demonstrate that chromogenic detection is more accurate than Northern dot-blotting.

TABLE I

| | Experimental Results | | |
|---|---|---|---|
| Probe Ratio | Microarray/CD | Northern Blotting | Probe Quantity |
| rca/rbcl = 4:1 | 3.1:1.0 | 1.6:1.0 | High quantity (1200:300) |
| rca/rbcL = 1:4 | 1.0:3.9 | 1.0:2.3 | Low quantity (120:480) |
| rca/rca = 10:1 | 6.2:1.0 | 3.7:1.0 | Large difference (1200:120) |
| rbcL/rbcL = 1:1.6 | 1.0:1.9 | 1.0:1.0 | Small difference (300:480) |

Numbers in parenthesis are the approximate number of control gene molecules spiked per cell.

The rca/rbcL results indicate that the response range of the Northern reached saturation at high gene transcript numbers such that the probe ratio of the two genes was compressed. In fact, the apparent linear relationship of probe number to chromogenic output in this range makes any interpretation of results here much easier than if Northern blotting is used instead.

The detection limit of the system was about 50 million molecules. For gene expression quantitation using $10^6$ cells, the detection limit of the system was therefore tens of transcripts per cell. On average, 25% of the cellular mRNA mass consists of transcripts expressed at less than 5 copies per cell. To detect gene transcripts at this level, $10^7$ cells may be necessary to achieve detection limit by the present protocol.

Since all that is required in this assay is that the chromogenic signals are proportional to the number of probes bound to the membrane after hybridization, a variety of labeling procedures can be used, including random-primed and end labelling. However, it is preferred that end-labeling be used.

EXAMPLE 2

This example illustrates how the methods of this invention can be used to identify differentially expressed genes.

Membranes containing an array of immobilized gene targets which has been hybridized to labeled probes from two mRNA sources can be prepared and used in the following manner.

Human lung adenocarcinoma cell lines CL1-0 and CL1-5 were grown in RPMI medium with 10% FBS and incubated at 37° C., 20% $O_2$, and 5% $CO_2$. These cells were used as mRNA sources and are described in Chu et al., Am J Respir Cell Mol Biol 17:353–360 (1997).

Normal human lung cDNA samples, obtained as a commercial cDNA library constructed on the Uni-ZAP XR phage vector (Stratagene, La Jolla, Calif.), were used to prepare the target DNA. The inserts averaging 1 kb in length were prepared by in vivo excision from the phage genome. To plate the rescued phagemids, 200 µl of SOLR bacteria (Stratagene) (O.D. at 600 nm=1) and an aliquot of the phage stock were mixed and incubated at 37° C. for 15 min. 50 µl of the above mixture were plated on Blue/White color selection plates containing LB broth, 1.5% agarose, 50 µg/ml ampicillin, 0.5 mM IPTG (isopropyl-1-thio-β-D-galactoside), and 20 µg/ml X-gal (5-bromo-4-chloro-3-indolyl-β-D-galactoside, obtainable from Sigma as product no. B4527; see Horwitz et al., J Med Chem 7:574 [1964]). After growth at 37° C. overnight, the colonies were picked from the selection plates and inoculated in 96-well microtiter plates containing 100 µl LB medium and 50 µg/ml of ampicillin. The liquid cultures were incubated at 37° C. overnight with gentle shaking. 1 µl of bacteria culture from each well of the 96-well plates was deposited in one well of a "V"-bottomed 96-well polycarbonate microtiter plate and amplified by PCR using the universal primers described in Example 1. The PCR conditions were as following: first cycle, 94° C. for 5 min, 68° C. for 5 min; second to seventeenth cycle, 94° C. for 30 sec, 68° C. for 5 min; eighteenth to thirty-fifth cycle, 94° C. for 30 sec, 68° C. for 5 min with a 15 sec increment each cycle. Other conditions for PCR and preparation of the samples for hybridization were as described in Example 1.

The three plant genes, lhc I, rbcL, and rca; and one human GAPDH (Glyceraldehyde-3-phosphate dehydrogenase) gene were amplified from tobacco cells or human adenocarcinoma cells as described in Example 1.

In order to study the interactions of known cellular genes in cells under stress or external stimulation, putative gene clones were obtained from the IMAGE consortium as described in Example 1. These gene were derived from various tissues and cloned into different library constructs. Most of the clones have been partially sequenced and the sequence information is available as expressed sequence tags (EST) from dbEST (Boguski et al., Nat Genet 4:332–333 [1993]) or GenBank (Benson et al., Nucleic Acids Res 22:3441–3444 [1994]). The cDNA clones and genes were amplified as described in Example 1.

To prepare hybridization probes, messenger RNAs were extracted from the two human lung adenocarcinoma cell lines, CL1-0 and CL1-5, by the method described in Example 1. 1 μg of CL1-0 mRNA was labeled with biotin, and 1 μg of CL1-5 mRNA was labeled with digoxigenin. The labeling reactions were done via incorporation by reverse transcription in the presence of 6 μM random primers, 0.5 mM each of DATP, dCTP, dGTP, 40 μM dTTP, 40 μM biotin-16-dUTP or 40μM digoxigenin-11-dUTP (Boehringer Mannheim), 10 mM DTT, 0.5 unit/μl RNasin (GIBCO-BRL), and 200 units of MuMLV reverse transcriptase (GIBCO-BRL). The 50 μl reaction mixture was incubated at 40° C. for 90 min and was stopped by heating the reaction mixture to 99° C. for 5 min. Residual RNA was degraded by adding 5.5 μl of 3 M NaOH followed by a 30-min incubation at 50° C., and the labeled samples were neutralized by adding 5.5 μl of 3 M acetic acid. The single-stranded cDNA probes were precipitated by adding 50 μl of 7.5 M ammonium acetate, 20 μg of linear polyacrylamide as carrier, 375 μl of absolute alcohol, and water to obtain a total volume of 525 μl.

The membrane carrying the double-stranded cDNA targets was pre-hybridized in hybridization buffer (5×SSC, 0.1% N-laurylsarcosine, 0.1% SDS, 1% BM blocking reagent, and 50 μg/ml salmon sperm DNA) at 68° C. for 1 hour. The two cDNA probes were mixed in equal proportions in 10 μl hybridization buffer containing 200 μg/ml $d(A)_{10}$ and 300–400 μg /ml of human COT-1 DNA to prevent non-specific binding, and hybridized to the normal lung cDNA fragments on the membrane by Southern hybridization procedures according to Sambrook et al., Id. The labeled cDNAs from the two cancer cell lines were sealed with the membrane in a assembly (SureSeal, Hybaid, Middlesex, UK) attached to a weight, and incubated at 95° C. for 2 min then at 68° C. for 12 hours. The membrane was then washed with 2×SSC containing 0.1% SDS for 5 min at room temperature followed by 3 washes with 0.1×SSC containing 0.1% SDS at 65° C. for 15 min each.

After hybridization, the membrane was blocked by 1% BM blocking reagent containing 2% dextran sulphate at room temperature for 1 hour and then rinsed with 1×TBS buffer solution (10 mM Tris-HCl [pH 7.4] and 150 mM NaCl) containing 0.3% BSA. To detect the spots on the membrane, streptavidin/β-galactosidase enzyme conjugate and anti-digoxigenin/alkaline phosphatase antibody-enzyme conjugate were employed. The detection can also be done in single-color mode. In this case, either one of the antibody/enzyme conjugates can be used. The membrane was incubated with a mixture containing 700×diluted streptavidin-β-galactosidase (GIBCO-BRL), 10,000×diluted anti-DIG-AP (Boehringer Mannheim), 4% polyethylene glycol 8000 (Sigma, St. Louis, Mo.), and 0.3% BSA in 1×TBS buffer for 2 hours. The chromogens were generated by first treating the membrane with X-gal solution, a β-galactosidase substrate, containing 1.2 mM X-gal, 1 mM $MgCl_2$, 3 mM $K_3Fe(CN)_6$, 3 mM $K_4Fe(CN)_6$ in 1×TBS buffer for 45 min at 37° C. The membrane was then briefly rinsed with deionized water and stained with Fast Red TR/Naphthol AS-MX substrate (Pierce, Rockford, USA; also obtainable from Sigma as product no. F4648), a alkaline phosphatase substrate. The color development reactions were then stopped by 1×PBS containing 20 mM EDTA. After color development, the cDNA molecules labeled with biotin yielded a blue chromogen and the cDNA molecules labeled with digoxigenin yielded a red chromogen. To determine the results from arrays of different densities, we performed image digitization using three different types of imaging devices that are commonly available to research laboratories: a flatbed scanner (Scanjet 4 c, Hewlett Packard, Palo Alto, Calif.), a color video camera (JVC TK-880U, Tokyo, Japan) attached to a copy stand, and a digital camera (DCS-420, Kodak, Rochester, N.Y.) attached to a stereomicroscope (Zeiss, Stemi 2000 C, Germany). The flatbed scanner, which was the least expensive, digitized the images at 600 dots-per-inch (dpi). Although the scanner did not provide presentation quality images for spots with diameters on the order of 200 μm, it did provide sufficient image resolution for quantitation purposes. The digital camera had the highest resolution of all the devices we tested and was used to digitize spots with diameter on the order of 100 μm or less. The colors of the spots were then separated into the artists' subtractive primaries (cyan, magenta, and yellow) and quantified by computer.

Most of the spots appeared purple indicating the presence of genes commonly expressed in the two cell lines. However, some spots exhibit more distinctive colors, either redder or bluer, which was used as an indication of differentially expressed genes in the two cell lines. The gene expression pattern was reproduced in repeated experiments.

The 3-D scatter plot of FIG. 1 is a quantitative representation of the spots on the membrane described immediately above and demonstrates how the system identifies differentially expressed genes. The color of each spot on the membrane is represented in the 3-D space by the position of the ball representing the spot. As seem in FIG. 1, most of the balls cluster along the solid line, which indicates that most of the spots on the membrane have the same proportion of the three subtractive primary colors but of different intensities. Some balls lie farther away from the line than others. These outlying balls represent the spots that are composed of unequal amounts of the labeled cDNA from the two cell lines, which suggests that the target gene is differentially expressed in the two cell lines. Therefore, by closing in the threshold planes (represented by the dashed lines) in the color space towards the regression (solid) line of the sample population, the computer program can pick out and register, one by one, the spots of a particular color intensity and composition, thereby identifying particular spots as outliers, for example, spots (H,8) and (E,7) which represent putative differentially expressed genes.

To determine optimal threshold planes such that a false positive error is less likely, an analysis of the experimental error was performed. In this context, a false positive error refers to counting a gene as differentially expressed when, in fact, it is not differentially expressed. To calibrate the standard error range of the system, cDNA molecules derived from the CL1-0 cell line were split in halves, one half labeled with biotin and the other half labeled with digoxigenin. The two halves were mixed in equal proportions and hybridized to the target cDNA molecules on the membrane. The standard error (defined as the square root of [variance/number of observations]) of the system was then estimated from this control experiment. For analysis on paper, the line regressed from the 96 data points are flanked by lines define the edges of the 99% prediction interval for the systematic error. Spots lying beyond the 99% prediction interval can be observed. These spots are significant enough to be registered as candidate differentially expressed genes.

To quantify the expression levels of known genes in a cell, the labeling procedure described above was modified to improve accuracy. For such an application, three plant genes were included in cDNA probe preparations during reverse transcription. The concept and procedures are described as follows.

In order to estimate the relative number of gene transcripts in a cell, the RNA extraction efficiency was taken into account. For this purpose, a known amount of lhc I poly-adenylated RNA was included in a suspension of $10^6$ cells and subjected to cell lysis, RNA extraction, reverse transcription, and labeling along with the rest of the sample. To calculate the extraction efficiency, a known amount of rbcL poly-adenylated RNA was added to the sample after the RNA extraction. The extraction efficiency could then be calculated from the chromogenic signals produced by the two plant gene probes. A known amount of biotin labeled cDNA of a third chloroplast gene, rca, was included in the probe solution before hybridization to determine the labeling efficiency. The rca gene was also used to normalize the signals on different membranes.

To obtain expression patterns in a different cell types or in the same cell type under different environments, the lhc I, rbcL, and rca plant control genes were deposited on one membrane. The expression level of a particular gene was calculated by reference to the CMY component of the control spots. As an illustration of the method and to simplify the data analysis, single color analysis was used in this experiment, the results of which are shown in Table II.

TABLE II

| Gene | Transcript Copy Number | |
|---|---|---|
| | CL1-0 | CL1-5 |
| RCA | 1000 | 1000 |
| rbcL | 762 | 762 |
| LHC-I | 579 | 554 |
| BRCA1 | 261 | 375 |
| oxa1 | 654 | 660 |
| APC | 104 | 273 |
| c-fos | 517 | 1007 |
| NAT | 84 | 314 |
| bcl-2 | 45 | 151 |
| IGF-2 | 5 | 69 |
| c-myb | 64 | 110 |
| c-myc | 871 | 946 |
| EGF | 143 | 232 |
| sis | 5 | 89 |
| WAF-1 | 261 | 946 |
| PML-1 | 13 | 21 |
| src | 438 | 151 |
| int-2 | 25 | 53 |
| GADPH | 2915 | 2904 |
| rck | 241 | 212 |
| N-ras | 281 | 277 |
| K-ras | 264 | 228 |
| pleckstrin | 123 | 151 |
| N-myc | 104 | 69 |
| PKCβ-1 | 261 | 558 |
| cyclin D1 | 104 | 191 |
| erbB-2 | 340 | 334 |
| HUMRBS | 45 | 8 |
| c-rel | 202 | 191 |
| c-jun | 320 | 436 |
| ros | 143 | 69 |
| msh-2 | 163 | 89 |
| mlh-1 | 1348 | 1242 |
| L-myc | 45 | 8 |
| c-cbl | 25 | 110 |
| nm23 | 1952 | 1496 |
| p53 | 143 | 28 |
| DPC4 | 635 | 252 |
| eIF4-E | 25 | 49 |
| H-ras-1 | 536 | 620 |
| E-cadherin | 98 | 4 |
| EGF-R | 84 | 69 |
| cyclin E | 5 | 69 |
| TNF-R | 84 | 171 |
| CYP2C19 | 78 | 2 |
| c-abl | 713 | 640 |

TABLE II-continued

| Gene | Transcript Copy Number | |
|---|---|---|
| | CL1-0 | CL1-5 |
| Surfactant Pro A | 143 | 110 |
| Ubiquitin Pro | 23 | 42 |

The CDNA molecules extracted from CL1-0 and CL1-5 were labeled with biotin as described above. Duplicate membranes carrying the same target gene fragments were hybridized with labeled cDNA probes derived from CL1-0 and CL1-5.

The nm23 gene is relatively over-expressed in CL1-0 cells while the PKC-β1 gene is relatively overexpressed in CL1-5 cells. These observations are consistent with previous findings which show that suppression of the nm23 gene leads to higher metastatic potential (Steeg et al., Cancer Res 48:6550–6554 [1988]) and that PKC-β1 is relatively over-expressed in the invasive cells (Schwartz et al., J Natl Cancer Inst 85:402–407 [1993]).

EXAMPLE 3

This example illustrates how the methods of this invention was used to identify genes correlated with tumor cell invasion ability.

500 genes selected from the IMAGE consortium human cDNA libraries were used as target DNA as previously described in Example 2. The probes were derived from human adenocarcinoma cell lines CL1-0, CL1-1, and CL1-5, each of increasing invasive ability, respectively. The cDNA representing the mRNA extracted from these cell lines were labeled with digoxigenin and the assay performed as in Example 2. Out of the 500 genes examined, seven genes appeared to correlate with invasiveness (Table III).

TABLE III

| Gene | Expreseion Level (Arbitrary Units) | | |
|---|---|---|---|
| | CL1-0 | CL1-1 | CL1-5 |
| sp2 TF | 6.4 | 2.7 | 0.5 |
| RAF | 17.0 | 16.0 | 3.7 |
| EDNRB | 15.5 | 13.0 | 5.0 |
| ALOX12 | 13.8 | 5.0 | 1.3 |
| nm23 | 11.9 | 10.6 | 3.1 |
| int-2 | 13.5 | 10.4 | 2.1 |
| γc precursor | 10.1 | 4.5 | 2.1 |

To determine if these same seven genes correlate with invasiveness in other mRNA samples, mouse melanoma cell lines B16F0, B16 F1, and B16F10, each with increasing tumor invasion capacity, were next tested. Out of the same 500 genes examined, 15 genes (see Table IV) appeared to correlate with invasiveness.

TABLE IV

| Gene | Expression Level (Arbitrary Units) | | |
|---|---|---|---|
| | B16-F0 | B16-F1 | B16-F10 |
| cyclin A1 | 9836 | 5374 | 3042 |
| HDLC1 | 7301 | 4137 | 3964 |
| Tyr Kinase | 3133 | 703 | 461 |
| Prohibitin | 4649 | 1860 | 1481 |

TABLE IV-continued

| Gene | Expression Level (Arbitrary Units) | | |
|---|---|---|---|
| | B16-F0 | B16-F1 | B16-F10 |
| Gu4 | 2723 | 1740 | 1108 |
| RAF | 8746 | 8182 | 3949 |
| v-kit | 3407 | 1922 | 1538 |
| HSP70 | 3503 | 3057 | 2405 |
| Villin 2 | 13244 | 2448 | 1844 |
| Keratin 5 | 10,326 | 2271 | 295 |
| N-ras | 8969 | 4337 | 3058 |
| RBAPN | 6464 | 5384 | 3015 |
| eIF4-E | 4416 | 3495 | 1655 |
| H-ras-1 | 7509 | 3601 | 2937 |
| nm23 | 4157 | 2487 | 1369 |

Inspecting the identity of the gene hits in Tables III and IV, only one gene, the nm23 gene, was found to correlate with invasiveness in both systems. As it is known that the nm23 gene is a metastasis suppressor gene, the result immediately above demonstrates that the microarray/CD can be used to isolate valid differentially expressed genes.

EXAMPLE 4

This example illustrates how the methods of this invention was used to identify differentially expressed genes in the same cell under different growth conditions.

To study the effect of external stimulants such as drugs or chemicals on gene expression, human trachea epithelial cells were grown with or without vitamin A acid (retinoic acid) in culture and used as mRNA sources. Table V lists genes differentially expressed when the cells were grown with or without vitamin A.

TABLE V

| Gene | Expression Level (Arbitrary Units) | |
|---|---|---|
| | Vitamin A− | Vitamin A+ |
| MMP-1 | 16 | 141 |
| PTP-Z | 18 | 83 |
| Gro2 | 7 | 32 |
| PCNA | 6 | 26 |
| NERF-2 | 7 | 28 |
| CD71 | 15 | 57 |
| DPC4 | 23 | 81 |
| ELGF | 15 | 51 |
| AMF-R | 12 | 40 |
| EGF-R | 51 | 158 |
| NAIP | 9 | 28 |
| Ear-1 | 103 | 30 |
| L-myc | 15 | 4 |
| Ras-like protein | 132 | 18 |

Other Embodiments

It is to be understood that while the invention has been described in conjunction with the detailed description, the foregoing description is intended to illustrate and not limit the scope of the invention, which is defined by the scope of the claims. other aspects, advantages, and modifications are within the scope of this invention.

For example, the computer program used to practice the methods of this invention can include algorithms for image processing and analysis, object recognition, color separation, and color filtering. Alternatively, patterns of gene expression can be visually inspected by the human eye. In addition, since the DNA on solid supports, such as a nylon membrane, can be preserved indefinitely, the genes of interest can be retrieved from the colored cDNA spots for further analysis such as sequencing.

What is claimed is:

1. A method of detecting a differentially expressed gene, comprising:

(a) providing a first sample of nucleic acids representing a first population of RNA transcripts and a second sample of nucleic acids representing a second population of RNA transcripts;

(b) labeling the nucleic acids in the first sample with a first member of a first specific binding pair, and labeling the nucleic acids in the second sample with a first member of a second specific binding pair;

(c) hybridizing the labeled nucleic acids in each sample to an excess of copies of a gene-specific sequence from a DNA library;

(d) labeling the hybridized nucleic acids in each sample by binding a second member of said first specific binding pair to the first member of said first specific binding pair, and binding a second member of the second specific binding pair to the first member of said second specific binding pair, wherein the second member of said first specific binding pair has an activity to convert a first chromogenic substrate into a first chromogen and the second member of said second specific binding pair has an activity to convert a second chromogenic substrate into a second chromogen, and wherein the first chromogen is of a color different from the second chromogen;

(e) contacting the first chromogenic substrate and the second chromogenic substrate with the second member of said first specific binding pair and the second member of said second specific binding pair, thereby converting the first chromogenic substrate and the second chromogenic substrate into the first chromogen and the second chromogen, respectively; and (f) determining amounts of the first chromogen and the second chromogen relative to each other in a mixture comprising the first chromogen and second chromogen by separating the color of the mixture into at least three primary colors; wherein a difference in the amounts of the first chromogen and the second chromogen in the mixture indicates that the gene-specific sequence is differentially expressed in the first population of RNA transcripts and the second population of RNA transcripts.

2. The method of claim 1, wherein the nucleic acids in the first sample and the nucleic acids in the second sample are mixed together after step (b) is performed and wherein the color of the first chromogen is different from the color of the second chromogen.

3. The method of claim 2, wherein the nucleic acids in the first sample and the nucleic acids in the second sample are end-labeled in step (b).

4. The method of claim 3, wherein the first chromogenic substrate is X-gal.

5. The method of claim 3, wherein the first chromogenic substrate is Fast Red TR and Naphthol AS-MX.

6. The method of claim 3, wherein the first member of the first specific binding pair is biotin.

7. The method of claim 3, wherein the first member of the first specific binding pair is digoxigenin.

8. The method of claim 1, wherein the nucleic acids in the first sample and the nucleic acids in the second sample are internally labeled in step (b).

9. The method of claim 8, wherein the first chromogenic substrate is X-gal.

10. The method of claim 8, wherein the first chromogenic substrate is Fast Red TR and Naphthol AS-MX.

11. The method of claim 8, wherein the first member of the first specific binding pair is biotin.

12. The method of claim 8, wherein the first member of the first specific binding pair is digoxigenin.

* * * * *

SEQUENCE LISTING

<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<221> NAME/KEY: misc_feature
<222> LOCATION: (1)...(25)
<223> OTHER INFORMATION: primer sequences for cloning by PCR

<400> SEQUENCE: 1
tagaactagt ggatcccccg ggctg                                    25

<210> SEQ ID NO 2
<211> LENGTH: 25
<212> TYPE: DNA
<213> ORGANISM: Artificial Sequence
<220> FEATURE:
<221> NAME/KEY: misc_feature
<222> LOCATION: (1)...(25)
<223> OTHER INFORMATION: primer sequences for cloning by PCR

<400> SEQUENCE: 2
tcactatagg gcgaattggg taccg                                    25

```
<210> SEQ ID NO 3
<211> LENGTH: 27
<212> TYPE: DNA
<213> ORGANISM: Artificial Sequence
<220> FEATURE:
<221> NAME/KEY: misc_feature
<222> LOCATION: (1)...(27)
<223> OTHER INFORMATION: primer sequences for cloning by PCR

<400> SEQUENCE: 3
aggaaacagc tatgaccatg attacgc                                        27

<210> SEQ ID NO 4
<211> LENGTH: 25
<212> TYPE: DNA
<213> ORGANISM: Artificial Sequence
<220> FEATURE:
<221> NAME/KEY: misc_feature
<222> LOCATION: (1)...(25)
<223> OTHER INFORMATION: primer sequences for cloning by PCR

<400> SEQUENCE: 4
ggttttccca gtcacgacgt tgtaa                                          25

<210> SEQ ID NO 5
<211> LENGTH: 26
<212> TYPE: DNA
<213> ORGANISM: Artificial Sequence
<220> FEATURE:
<221> NAME/KEY: misc_feature
<222> LOCATION: (1)...(26)
<223> OTHER INFORMATION: primer sequences for cloning by PCR

<400> SEQUENCE: 5
tacgactcac tatagggaat ttggcc                                         26

<210> SEQ ID NO 6
<211> LENGTH: 25
<212> TYPE: DNA
<213> ORGANISM: Artificial Sequence
<220> FEATURE:
<221> NAME/KEY: misc_feature
<222> LOCATION: (1)...(25)
<223> OTHER INFORMATION: primer sequences for cloning by PCR

<400> SEQUENCE: 6
gccagtgcca agctaaaatt aaccc                                          25
```